United States Patent
Maskara et al.

(10) Patent No.: US 10,172,536 B2
(45) Date of Patent: Jan. 8, 2019

(54) REAL-TIME FEEDBACK FOR ELECTRODE CONTACT DURING MAPPING

(71) Applicant: Boston Scientific Scimed Inc., Maple Grove, MN (US)

(72) Inventors: Barun Maskara, Princeton Jct, NJ (US); Pramodsingh H. Thakur, Woodbury, MN (US); Shantha Arcot-Krishnamurthy, Sammamish, WA (US); Shibaji Shome, Arden Hills, MN (US); Sunipa Saha, Shoreview, MN (US); Allan C. Shuros, St. Paul, MN (US); Scott A. Meyer, Lakeville, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 139 days.

(21) Appl. No.: 15/220,066

(22) Filed: Jul. 26, 2016

(65) Prior Publication Data
US 2016/0331267 A1 Nov. 17, 2016

Related U.S. Application Data

(63) Continuation of application No. 14/136,607, filed on Dec. 20, 2013, now Pat. No. 9,427,167.
(Continued)

(51) Int. Cl.
*A61B 5/00* (2006.01)
*A61B 5/053* (2006.01)
(Continued)

(52) U.S. Cl.
CPC ............ *A61B 5/0538* (2013.01); *A61B 5/044* (2013.01); *A61B 5/0422* (2013.01);
(Continued)

(58) Field of Classification Search
CPC ..... A61B 5/044; A61B 5/0422; A61B 5/0424; A61B 5/6858; A61B 5/6885; A61B 5/053; A61B 5/0538
See application file for complete search history.

(56) References Cited

U.S. PATENT DOCUMENTS

| | | | |
|---|---|---|---|
| 5,383,874 A | 1/1995 | Jackson et al. | |
| 5,398,683 A | 3/1995 | Edwards et al. | |

(Continued)

FOREIGN PATENT DOCUMENTS

| | | | |
|---|---|---|---|
| CN | 101066225 A | 11/2007 | |
| CN | 102131458 A | 7/2011 | |

(Continued)

OTHER PUBLICATIONS

"Frequency-Division Multiplexing", Wikipedia, the Feree Encyclopedia, Printed May 20, 2013. <http://en.wikipedia.org/wiki/Frequency-division_multiplexing>.
"Time-Division_Multiplexing", Wikipedia, the Free Encyclopedia, Printed May 20, 2013. <http://en.wikipedia.org/wiki/Time-division-multiplexing>.
International Preliminary Report on Patentability issued in PCT/US2013/077019, dated Jun. 23, 2015, 8 pages.
(Continued)

*Primary Examiner* — Max Hindenburg
(74) *Attorney, Agent, or Firm* — Faegre Baker Daniels LLP

(57) ABSTRACT

A catheter system includes a mapping catheter including a plurality of mapping electrodes, each mapping electrode configured to sense signals associated with an anatomical structure. The catheter system further includes a processor operatively coupled to the plurality of mapping electrodes and configured to receive the signals sensed by the plurality of mapping electrodes, characterize the signals sensed by the plurality of mapping electrodes based on a signal parameter
(Continued)

of the sensed signals, and generate an output of a quality of contact of the plurality of mapping electrodes with the anatomical structure based on the signal characterization.

15 Claims, 4 Drawing Sheets

Related U.S. Application Data

(60) Provisional application No. 61/739,980, filed on Dec. 20, 2012.

(51) Int. Cl.
  *A61B 5/044* (2006.01)
  *A61B 5/042* (2006.01)
  *A61B 5/0424* (2006.01)
  *A61B 18/14* (2006.01)
  *A61B 17/00* (2006.01)
  *A61B 18/00* (2006.01)
  *A61B 90/00* (2016.01)

(52) U.S. Cl.
  CPC .......... *A61B 5/0424* (2013.01); *A61B 5/6858* (2013.01); *A61B 5/6885* (2013.01); *A61B 18/1492* (2013.01); *A61B 2017/00044* (2013.01); *A61B 2017/00053* (2013.01); *A61B 2018/00267* (2013.01); *A61B 2018/00678* (2013.01); *A61B 2018/00839* (2013.01); *A61B 2090/065* (2016.02)

(56) References Cited

U.S. PATENT DOCUMENTS

| | | | |
|---|---|---|---|
| 5,437,664 A | 8/1995 | Cohen et al. | |
| 5,447,529 A | 9/1995 | Marchlinski et al. | |
| 5,562,721 A | 10/1996 | Marchlinski et al. | |
| 5,598,848 A | 2/1997 | Swanson et al. | |
| 5,647,870 A | 7/1997 | Kordis et al. | |
| 5,722,401 A | 3/1998 | Pietroski et al. | |
| 5,820,568 A | 10/1998 | Willis | |
| 5,836,990 A | 11/1998 | Li | |
| 5,840,031 A | 11/1998 | Crowley | |
| 5,935,079 A * | 8/1999 | Swanson | A61B 5/0422 600/374 |
| 6,050,267 A | 4/2000 | Nardella et al. | |
| 6,056,745 A | 5/2000 | Panescu et al. | |
| 6,063,078 A | 5/2000 | Wittkampf | |
| 6,070,094 A | 5/2000 | Swanson et al. | |
| 6,183,468 B1 | 2/2001 | Swanson et al. | |
| 6,233,491 B1 | 5/2001 | Kordis et al. | |
| 6,391,024 B1 | 5/2002 | Sun et al. | |
| 6,546,270 B1 | 4/2003 | Goldin et al. | |
| 6,569,160 B1 | 5/2003 | Goldin et al. | |
| 6,584,345 B2 | 6/2003 | Govari | |
| 6,663,573 B2 | 12/2003 | Goldin | |
| 6,735,465 B2 | 5/2004 | Panescu | |
| 6,804,545 B2 | 10/2004 | Fuimaono et al. | |
| 6,845,257 B2 | 1/2005 | Fuimaono et al. | |
| 6,950,689 B1 | 9/2005 | Willis et al. | |
| 7,099,711 B2 | 8/2006 | Fuimaono et al. | |
| 7,123,951 B2 | 10/2006 | Fuimaono et al. | |
| 7,181,262 B2 | 2/2007 | Fuimaono et al. | |
| 7,610,073 B2 | 10/2009 | Fuimaono et al. | |
| 7,662,151 B2 | 2/2010 | Crompton et al. | |
| 7,720,420 B2 | 5/2010 | Kajita | |
| 7,879,029 B2 | 2/2011 | Jimenez | |
| 7,894,871 B2 | 2/2011 | Wittkampf et al. | |
| 7,938,828 B2 | 5/2011 | Koblish | |
| 7,976,541 B2 | 7/2011 | McGee et al. | |
| 7,996,085 B2 | 8/2011 | Levin | |
| 8,048,063 B2 * | 11/2011 | Aeby | A61B 5/042 385/13 |
| 8,103,327 B2 | 1/2012 | Harlev et al. | |
| 8,160,690 B2 | 4/2012 | Wilfley et al. | |
| 8,162,935 B2 | 4/2012 | Paul et al. | |
| 8,208,991 B2 | 6/2012 | Markowitz et al. | |
| 8,265,745 B2 | 9/2012 | Hauck et al. | |
| 8,267,926 B2 | 9/2012 | Paul et al. | |
| 8,290,578 B2 | 10/2012 | Schneider | |
| 8,317,783 B2 | 11/2012 | Cao et al. | |
| 8,340,751 B2 | 12/2012 | Markowitz et al. | |
| 8,369,922 B2 | 2/2013 | Paul et al. | |
| 8,380,276 B2 * | 2/2013 | Schultz | A61B 5/042 600/374 |
| 8,400,164 B2 | 3/2013 | Osadchy et al. | |
| 8,403,925 B2 | 3/2013 | Miller et al. | |
| 8,406,866 B2 | 3/2013 | Deno et al. | |
| 8,449,535 B2 | 5/2013 | Deno et al. | |
| 8,454,538 B2 | 6/2013 | Wittkampf et al. | |
| 8,454,589 B2 | 6/2013 | Deno et al. | |
| 8,489,184 B2 | 7/2013 | Wilfley et al. | |
| 8,583,215 B2 | 11/2013 | Lichtenstein | |
| 8,603,084 B2 | 12/2013 | Fish et al. | |
| 8,603,085 B2 | 12/2013 | Jimenez | |
| 8,622,935 B1 * | 1/2014 | Leo | A61B 5/6843 600/585 |
| 8,644,950 B2 | 2/2014 | Hauck | |
| 8,672,936 B2 | 3/2014 | Thao et al. | |
| 8,679,109 B2 | 3/2014 | Paul et al. | |
| 8,728,077 B2 | 5/2014 | Paul et al. | |
| 8,755,860 B2 | 6/2014 | Paul et al. | |
| 8,906,011 B2 | 12/2014 | Gelbart et al. | |
| 8,998,890 B2 | 4/2015 | Paul et al. | |
| 9,125,565 B2 | 9/2015 | Hauck | |
| 9,149,327 B2 * | 10/2015 | Lambert | A61B 18/1492 |
| 9,168,004 B2 | 10/2015 | Gliner et al. | |
| 9,173,586 B2 | 11/2015 | Deno et al. | |
| 9,254,163 B2 | 2/2016 | Paul et al. | |
| 9,271,782 B2 | 3/2016 | Paul et al. | |
| 9,283,026 B2 | 3/2016 | Paul et al. | |
| 9,427,167 B2 | 8/2016 | Maskara et al. | |
| 9,510,786 B2 * | 12/2016 | Gliner | A61B 5/6852 |
| 9,681,923 B2 * | 6/2017 | Barley | A61B 90/06 |
| 2002/0068934 A1 | 6/2002 | Edwards et al. | |
| 2002/0128643 A1 | 9/2002 | Simpson et al. | |
| 2002/0165448 A1 | 11/2002 | Ben-Haim et al. | |
| 2005/0203375 A1 | 9/2005 | Willis et al. | |
| 2007/0181139 A1 | 8/2007 | Hauck | |
| 2007/0197929 A1 | 8/2007 | Porath et al. | |
| 2007/0265609 A1 | 11/2007 | Thapliyal et al. | |
| 2008/0161796 A1 | 7/2008 | Cao et al. | |
| 2008/0172049 A1 | 7/2008 | Bredno et al. | |
| 2008/0243214 A1 | 10/2008 | Koblish | |
| 2008/0281319 A1 | 11/2008 | Paul et al. | |
| 2008/0288038 A1 | 11/2008 | Paul et al. | |
| 2008/0312521 A1 | 12/2008 | Solomon | |
| 2008/0312713 A1 | 12/2008 | Wilfley et al. | |
| 2009/0093810 A1 | 4/2009 | Subramaniam et al. | |
| 2009/0163904 A1 | 6/2009 | Miller et al. | |
| 2009/0171345 A1 | 7/2009 | Miller et al. | |
| 2009/0177069 A1 | 7/2009 | Razavi | |
| 2009/0177111 A1 | 7/2009 | Miller et al. | |
| 2009/0209950 A1 | 8/2009 | Starksen | |
| 2009/0275827 A1 | 11/2009 | Aiken et al. | |
| 2009/0281541 A1 | 11/2009 | Ibrahim et al. | |
| 2009/0306643 A1 | 12/2009 | Pappone et al. | |
| 2010/0168557 A1 | 7/2010 | Deno et al. | |
| 2010/0241117 A1 | 9/2010 | Paul et al. | |
| 2010/0268059 A1 | 10/2010 | Ryu et al. | |
| 2010/0286550 A1 | 11/2010 | Harlev et al. | |
| 2011/0034915 A1 | 2/2011 | Ibrahim et al. | |
| 2011/0125150 A1 | 5/2011 | Deno et al. | |
| 2011/0137153 A1 | 6/2011 | Govari et al. | |
| 2011/0144509 A1 | 6/2011 | Kahlert et al. | |
| 2011/0237933 A1 | 9/2011 | Cohen | |
| 2012/0078129 A1 | 3/2012 | Bailin | |
| 2012/0136346 A1 | 5/2012 | Condie et al. | |
| 2012/0136348 A1 | 5/2012 | Condie et al. | |
| 2012/0150021 A1 | 6/2012 | Schwartz | |
| 2012/0184863 A1 | 7/2012 | Harlev et al. | |
| 2012/0184864 A1 | 7/2012 | Harlev et al. | |

(56) References Cited

U.S. PATENT DOCUMENTS

| | | |
|---|---|---|
| 2012/0184865 A1 | 7/2012 | Harlev et al. |
| 2012/0209174 A1 | 8/2012 | Moll et al. |
| 2012/0238897 A1 | 9/2012 | Wilfley et al. |
| 2012/0253161 A1 | 10/2012 | Harlev et al. |
| 2013/0023784 A1 | 1/2013 | Schneider et al. |
| 2013/0060245 A1 | 3/2013 | Grunewald et al. |
| 2013/0172875 A1 | 7/2013 | Govari et al. |
| 2013/0190717 A1 | 7/2013 | Dollar et al. |
| 2013/0190747 A1 | 7/2013 | Koblish et al. |
| 2013/0226169 A1 | 8/2013 | Miller et al. |
| 2014/0058375 A1 | 2/2014 | Koblish |
| 2014/0100563 A1 | 4/2014 | Govari et al. |
| 2014/0194867 A1 | 7/2014 | Fish et al. |
| 2014/0228713 A1 | 8/2014 | Thao et al. |
| 2014/0364843 A1 | 12/2014 | Paul et al. |
| 2014/0364848 A1 | 12/2014 | Heimbecher et al. |
| 2015/0005624 A1 | 1/2015 | Hauck et al. |
| 2016/0008065 A1 | 1/2016 | Gliner et al. |
| 2016/0242667 A1 | 8/2016 | Fay et al. |

FOREIGN PATENT DOCUMENTS

| | | |
|---|---|---|
| CN | 103379873 A | 10/2013 |
| WO | 2014036439 A2 | 3/2014 |

OTHER PUBLICATIONS

International Preliminary Report on Patentability issued in PCT/US2014/066427, dated Jun. 2, 2016, 7 pages.
International Search Report and Written Opinion issued in PCT/US2013/077019, dated Apr. 9, 2014, 13 pgs.
International Search Report and Written Opinion issued in PCT/US2014/066427, dated Apr. 7, 2015, 9 pages.
Gabriel, C., et al. The Dielectric Properties of Biological Tissues: I. Literature Survey. Phys. Med. Biol., 41:2231-2249, 1996.
International Search Report and Written Opinion issued in PCT/US2016/018689, dated Apr. 28, 2016, 11 pages.
International Preliminary Report on Patentability issued in PCT/US2016/018689, dated Aug. 31, 2017, 7 pages.

* cited by examiner

REAL-TIME FEEDBACK FOR ELECTRODE CONTACT DURING MAPPING

CROSS-REFERENCE TO RELATED APPLICATION

This application is a continuation of U.S. application Ser. No. 14/136,607, filed Dec. 20, 2013, which claims the benefit of Provisional Application No. 61/739,980, filed Dec. 20, 2012, all of which are incorporated herein by reference in their entirety.

TECHNICAL FIELD

The present disclosure relates to mapping systems. More particularly, the present disclosure relates to a mapping system configured to provide real-time feedback for mapping electrode contact with an anatomical structure during mapping.

BACKGROUND

Physicians make use of catheters in medical procedures to gain access into interior regions of the body for diagnostic and therapeutic purposes. It is important for the physician to be able to precisely position the catheter within the body to gain contact with a desired tissue location. During these procedures, a physician steers the catheter through a main vein or artery into the interior region of the heart that is to be treated. The physician then further manipulates a steering mechanism to place the electrode carried on the distal tip of the catheter into direct contact with the endocardial tissue. The physician directs energy from the electrode through myocardial tissue either to an indifferent electrode (in a unipolar electrode arrangement) or to an adjacent electrode (in a bi-polar electrode arrangement) to ablate the tissue.

Before ablating heart tissue, physicians often examine the propagation of electrical impulses in heart tissue to locate aberrant conductive pathways and to identify the arrhythmia foci, which are ablated. The techniques used to analyze these pathways and locate foci are commonly called mapping.

SUMMARY

Disclosed herein are various embodiments of methods for providing real-time feedback for mapping electrode contact with an anatomical structure during mapping, as well as cardiac mapping systems employing such methods.

In an Example 1, a catheter system comprising: a catheter including a plurality of mapping electrodes, each mapping electrode configured to sense signals associated with an anatomical structure; and a processor operatively coupled to the plurality of mapping electrodes and configured to: receive the signals sensed by the plurality of mapping electrodes; determine a signal parameter associated with each of the plurality of mapping electrodes; and determine a quality of contact of each of the plurality of mapping electrodes with the anatomical structure based on the signal parameter.

In an Example 2, the catheter system of Example 1, further comprising a display device configured to provide a graphical display representative of the quality of contact of the plurality of mapping electrodes.

In an Example 3, the catheter system of Example 1, the catheter further comprising a contact determination mechanism, wherein the processor is configured to determine the quality of contact based on the signal parameter and an output of the contact determination mechanism.

In an Example 4, the catheter system of Example 3, the contact determination mechanism comprising at least one of a force sensor and an impedance sensor.

In an Example 5, the catheter system of Example 1, wherein the processor is further configured to generate a map of the anatomical structure based on electrodes having sensed signals with amplitudes greater than a threshold amplitude.

In an Example 6, the catheter system of Example 1, wherein the processor is configured to sense and characterize at least one of unipolar signals and bipolar signals.

In an Example 7, the catheter system of Example 1, wherein the catheter comprises an ablation catheter.

In an Example 8, the catheter system of Example 1, wherein the processor is further configured to identify contours of the anatomical structure based on the quality of contact of the plurality of mapping electrodes.

In an Example 9, the catheter system of Example 1, wherein the processor is further configured to determine an orientation of the plurality of mapping electrodes based on the quality of contact of the plurality of mapping electrodes.

In an Example 10, a method for mapping an anatomical structure, the method comprising: sensing signals associated with an anatomical structure with a plurality of mapping electrodes; characterizing the signals sensed by the plurality of mapping electrodes based on a signal parameter associated with the plurality of mapping electrodes; determining a quality of contact of the plurality of mapping electrodes with the anatomical structure based on the signal characterization; and generating a map of the anatomical structure based only on electrodes having sensed signals with a quality of contact exceeding a threshold value.

In an Example 11, the method of Example 10, wherein the determining step comprises combining the signal characterization with an output of a contact determination mechanism.

In an Example 12, the method of Example 11, wherein the contact determination mechanism comprises at least one of a force sensor and an impedance sensor.

In an Example 13, the method of Example 10, further comprising generating a map of the anatomical structure based only on electrodes having sensed signals with amplitudes greater than a threshold amplitude.

In an Example 14, the method of Example 10, further comprising identifying contours of the anatomical structure based on the quality of contact of the plurality of mapping electrodes.

In an Example 15, the method of Example 10, further comprising determining an orientation of the plurality of mapping electrodes based on the quality of contact of the plurality of mapping electrodes.

In an Example 16, a method for mapping an anatomical structure, the method comprising: positioning a plurality of mapping electrodes proximate to an anatomical structure; sensing signals with the plurality of mapping electrodes; characterizing the signals sensed by the plurality of mapping electrodes based on a signal parameter associated with the mapping electrodes; determining a quality of contact of the plurality of mapping electrodes with the anatomical structure based on the signal characterization; displaying a graphical display representative of the quality of contact of the plurality of electrodes; repositioning the plurality of mapping electrodes with respect to the anatomical structure; and updating the graphical display in real-time as the quality of contact of the plurality of electrodes changes when the plurality of electrodes are repositioned.

In an Example 17, the method of Example 16, wherein the sensing step comprises sensing bipolar signals with the pairs of the plurality of mapping electrodes.

In an Example 18, the method of Example 16, wherein the sensing step comprises sensing unipolar signals with each of the plurality of mapping electrodes.

In an Example 19, the method of Example 16, and further comprising generating a map of the anatomical structure based only on electrodes having sensed signals with amplitudes greater than a threshold amplitude.

In an Example 20, the method of Example 16, wherein the determining step comprises combining the signal characterization with an output of a contact determination mechanism, the contact determination mechanism comprising at least one of a force sensor and an impedance sensor.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

Figure 1:
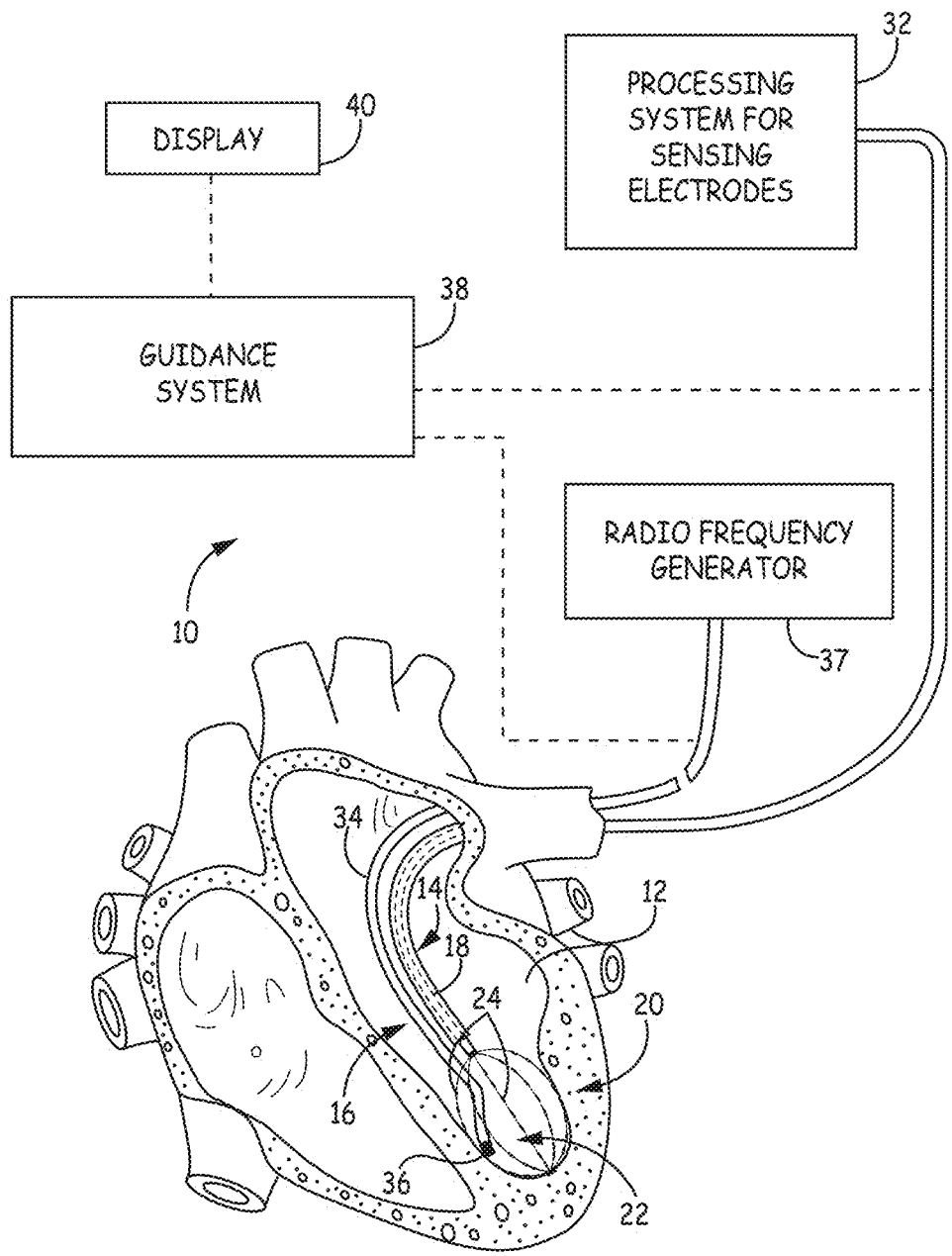
FIG. 1 is a schematic view of an embodiment of a system for accessing a targeted tissue region in the body for diagnostic and therapeutic purposes.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

FIG. 1 is a schematic view of a system 10 for accessing a targeted tissue region in the body for diagnostic or therapeutic purposes. FIG. 1 generally shows the system 10 deployed in the left ventricle of the heart. Alternatively, system 10 can be deployed in other regions of the heart, such as the left atrium, right atrium, or right ventricle. While the illustrated embodiment shows the system 10 being used for ablating heart tissue, the system 10 (and the methods described herein) may alternatively be configured for use in other tissue ablation applications, such as procedures for ablating tissue in the prostrate, brain, gall bladder, uterus, and other regions of the body, including in systems that are not necessarily catheter-based.

The system 10 includes a mapping probe 14 and an ablation probe 16. In FIG. 1, each is separately introduced into the selected heart region 12 through a vein or artery (e.g., the femoral vein or artery) through suitable percutaneous access. Alternatively, the mapping probe 14 and ablation probe 16 can be assembled in an integrated structure for simultaneous introduction and deployment in the heart region 12.

The mapping probe 14 has a flexible catheter body 18. The distal end of the catheter body 18 carries a three-dimensional multiple electrode structure 20. In the illustrated embodiment, the structure 20 takes the form of a basket defining an open interior space 22 (see FIG. 2), although other multiple electrode structures could be used. The multiple electrode structure 20 carries a plurality of electrodes 24 configured to sense intrinsic physiological activity in the anatomical region on which the ablation procedure is to be performed.

The electrodes 24 are electrically coupled to a processing system 32. A signal wire (not shown) is electrically coupled to each electrode 24 on the basket structure 20. The wires extend through the body 18 of the probe 14 and electrically couple the electrodes 24 to the processing system 32 and the guidance system 34. The electrodes 24 sense intrinsic electrical activity in heart tissue. The sensed activity is processed by the processing system 32 to assist the physician in identifying the site or sites within the heart appropriate for ablation.

In some embodiments, the processing system 32 may be configured to measure the intrinsic electrical activity in the heart tissue adjacent to the electrodes 24. For example, in some embodiments, the processing system 32 is configured to detect intrinsic electrical activity associated with a dominant rotor in the anatomical feature being mapped. Studies have shown that dominant rotors have a role in the initiation and maintenance of atrial fibrillation, and ablation of the rotor path and/or rotor core may be effective in terminating the atrial fibrillation. The processing system 32 processes the sensed information to derive the location of a site appropriate for ablation using the ablation probe 16.

The ablation probe 16 includes a flexible catheter body 34 that carries one or more ablation electrodes 36. The one or more ablation electrodes 36 are electrically connected to a radio frequency generator 37 that is configured to deliver ablation energy to the one or more ablation electrodes 36. The ablation probe 16 is movable with respect to the anatomical feature to be treated, as well as the structure 20. The ablation probe 16 is positionable between or adjacent to electrodes 24 of the structure 20 as the one or more ablation electrodes 36 are positioned with respect to the tissue to be treated.

A guidance system 38 is electrically coupled to the mapping catheter 14 and the ablation catheter 16. The guidance system 38 collects and processes information regarding the location of the ablation probe 16 within the space 22 defined by the basket structure 20, in term of its position relative to the position of the electrodes 24. The guidance system 38 provides a position-identifying output that aids the physician in guiding the ablation electrodes 36 into contact with tissue at the site identified for ablation. The guidance system 38 can process and provide position-specific information in various ways.

In the illustrated embodiment, the guidance system 38 includes an output display device 40 (e.g., a CRT, LED display, or a printer). In some embodiments, the display device 40 is configured to display a representation of the mapping catheter 14 and ablation catheter 16 relative to the anatomical structure.

Figure 2:
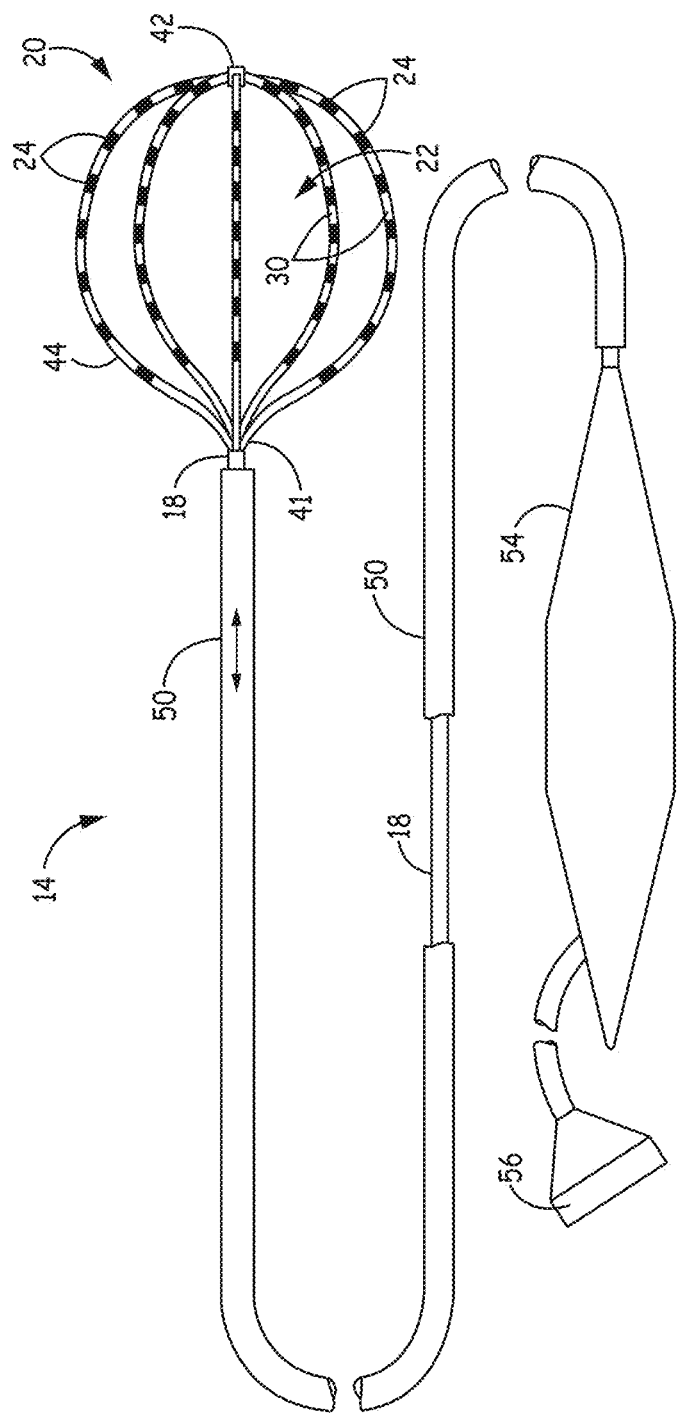
FIG. 2 is a schematic view of an embodiment of a mapping catheter having a basket functional element carrying structure for use in association with the system of FIG. 1.

FIG. 2 illustrates an embodiment of the mapping catheter 14 including electrodes 24 at the distal end suitable for use in the system 10 shown in FIG. 1. The mapping catheter 14 has a flexible catheter body 18, the distal end of which carries the three dimensional structure 20 configured to carry the mapping electrodes or sensors 24. The mapping electrodes 24 sense intrinsic electrical activity in the heart tissue, which sensed activity is then processed by the processing system 32 and guidance system 38 to assist the physician in identifying the site or sites having a heart rhythm disorder. This process is commonly referred to as mapping. This information can then be used to determine an appropriate location for applying appropriate therapy (e.g., ablation) to the identified sites, and to navigate the one or more ablation electrodes 36 to the identified sites.

The illustrated three dimensional structure 20 comprises a base member 41 and an end cap 42 between which flexible splines 44 generally extend in a circumferentially spaced relationship. As discussed above, the three dimensional structure 20 takes the form of a basket defining an open interior space 22. In some embodiments, the splines 44 are made of a resilient inert material, such as, e.g., Nitinol metal or silicone rubber, and are connected between the base member 41 and the end cap 42 in a resilient, pretensed condition, to bend and conform to the tissue surface they contact. In the illustrated embodiment, eight splines 44 form the three dimensional structure 20. Additional or fewer splines 44 could be used in other embodiments. As illustrated, each spline 44 carries eight mapping electrodes 24. Additional or fewer mapping electrodes 24 could be disposed on each spline 44 in other embodiments of the three dimensional structure 20. In the illustrated embodiment, the three dimensional structure 20 is relatively small (e.g., 40 mm or less in diameter). In alternative embodiments, the three dimensional structure 20 is larger (e.g., 40 mm in diameter or greater).

A slidable sheath 50 is movable along the major axis of the catheter body 30. Moving the sheath 50 forward (i.e., toward the distal end) causes the sheath 50 to move over the three dimensional structure 20, thereby collapsing the structure 20 into a compact, low profile condition suitable for introduction into an interior space, such as, for example, into the heart. In contrast, moving the sheath 50 rearward (i.e., toward the proximal end) frees the three dimensional structure 20, allowing the structure 20 to spring open and assume the pretensed position illustrated in FIG. 2. Further details of embodiments of the three dimensional structure 20 are disclosed in U.S. Pat. No. 5,647,870, entitled "Multiple Electrode Support Structures," which is hereby incorporated by reference in its entirety.

A signal wire (not shown) is electrically coupled to each mapping electrode 26. The wires extend through the body 30 of the mapping catheter 20 into a handle 54, in which they are coupled to an external connector 56, which may be a multiple pin connector. The connector 56 electrically couples the mapping electrodes 24 to the processing system 32 and guidance system 38. Further details on mapping systems and methods for processing signal generated by the mapping catheter are discussed in U.S. Pat. No. 6,070,094, entitled "Systems and Methods for Guiding Movable Electrode Elements within Multiple-Electrode Structure," U.S. Pat. No. 6,233,491, entitled "Cardiac Mapping and Ablation Systems," and U.S. Pat. No. 6,735,465, entitled "Systems and Processes for Refining a Registered Map of a Body Cavity," the disclosures of which are incorporated herein by reference.

It is noted that other multi-electrode structures could be deployed on the distal end. It is further noted that the multiple mapping electrodes 24 may be disposed on more than one structure rather than, for example, the single mapping catheter 14 illustrated in FIG. 2. For example, if mapping within the left atrium with multiple mapping structures, an arrangement comprising a coronary sinus catheter carrying multiple mapping electrodes and a basket catheter carrying multiple mapping electrodes positioned in the left atrium may be used. As another example, if mapping within the right atrium with multiple mapping structures, an arrangement comprising a decapolar catheter carrying multiple mapping electrodes for positioning in the coronary sinus, and a loop catheter carrying multiple mapping electrodes for positioning around the tricuspid annulus may be used.

Additionally, although the mapping electrodes 24 have been described as being carried by dedicated probes, such as mapping catheter 14, the mapping electrodes can be carried on non-mapping dedicated probes. For example, an ablation catheter (e.g., the ablation catheter 16) can be configured to include one or mapping electrodes 24 disposed on the distal end of the catheter body and coupled to the signal processing system 32 and guidance system 38. As another example, the ablation electrode at the distal end of the ablation catheter may be coupled to the signal processing system 32 and guidance system 38 to also operate as a mapping electrode.

Figure 3:
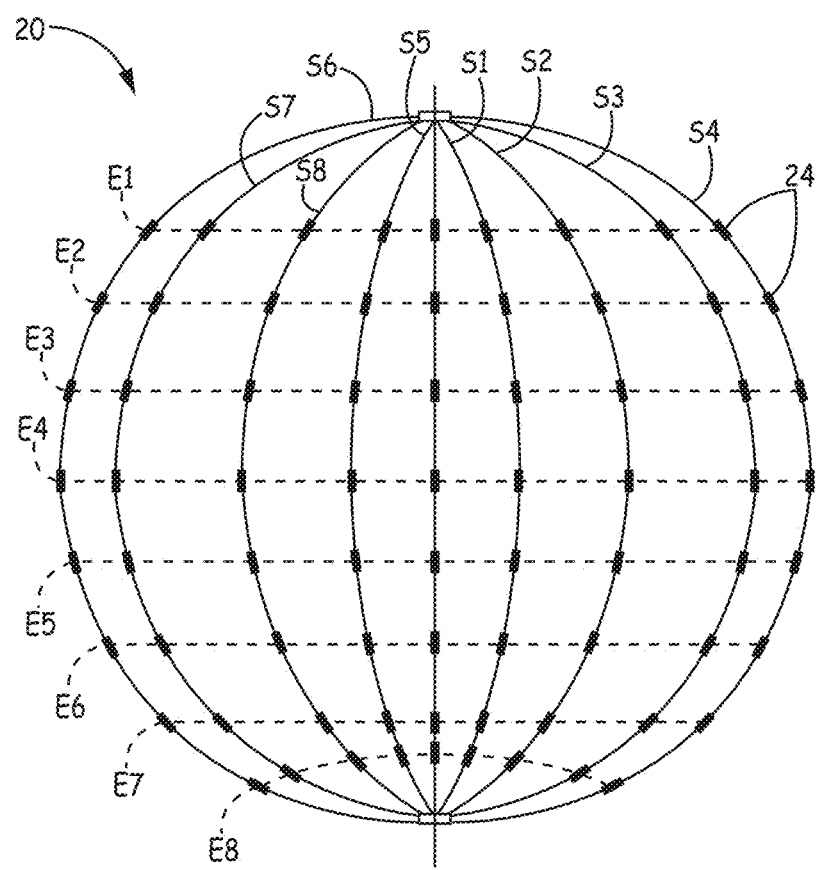
FIG. 3 is a schematic side view of an embodiment of the basket functional element including a plurality of mapping electrodes.

To illustrate the operation of the system 10, FIG. 3 is a schematic view of an embodiment of the basket structure 20 including a plurality of mapping electrodes 24 disposed on a plurality of splines 44. In the illustrated embodiment, the basket structure includes sixty-four mapping electrodes 24. The mapping electrodes 24 are disposed in groups of eight electrodes 24 (labeled E1, E2, E3, E4, E5, E6, E7, and E8) on each of eight splines 44 (labeled S1, S2, S3, S4, S5, S6, S7, and S8). While the sixty-four mapping electrodes 24 are shown disposed on a basket structure 20, the mapping electrodes 24 may alternatively be arranged in different numbers and on different structures.

When the basket structure 20 is introduced into the anatomical structure to be mapped (e.g., heart), some of the electrodes 24 are brought into contact with the anatomical structure to allow measurements of physiological activity in the anatomical structure. The physiological activity is then used to generate a map of the physiological activity in the anatomical structure to aid the clinician with diagnosis and treatment of the anatomical structure. However, because the contours of the anatomical structure may not correspond to the contours of the basket structure 20, some of the electrodes 24 in the basket structure 20 may make better contact with the anatomical structure than others of the electrodes 24. In order to assure quality data collection during mapping, the mapping system 10 according to the present disclosure is configured to provide the clinician with real-time feedback of electrode contact quality during the mapping process.

In some embodiments, the processing system 32 is configured to receive signals from each of the electrodes 24 and determine a quality of the contact of each of the electrodes 24 based on the received signals. In some embodiments, the processing system 32 measures bipolar signals based on sequential or simultaneous measurements across two of the electrodes 24 in the basket structure 20. For example, the processing system 32 may measure signals across adjacent electrodes 24 (e.g., E1-E2, E3-E4, E5-E6, E7-E8) on the same spline (S1-S8). In some embodiments, the processing system measures unipolar signals based on sequential or simultaneous signal measurements by each of the electrodes 24 individually.

The processing system 32 can be configured to establish the quality of contact of the electrodes 24 by characterizing the measured signals from the electrodes 24. For example, in some embodiments, the quality of contact of each of the mapping electrodes 24 is a function of the amplitude of the signal measured by the electrode 24 (i.e., higher signal amplitude correlates to better contact). As another example, the quality of contact of each of the mapping electrodes 24 is a function of the frequency distribution of the signals measured by the electrodes 24. More specifically, signals with a higher frequency component in bipolar measurements can be identified as channels making good contact with the anatomical structure. In some embodiments, the electrodes having a measured signal parameter that exceeds a threshold or falls within a predetermined range are identified as making good contact with the anatomical structure (i.e., contact sufficient to provide reliable mapping data). The signal measurements to determine quality of contact can be combined with other contact determination mechanisms, such as force and/or impedance sensors, that may be integrated onto the basket structure 20.

The processing system 32 can be configured to provide an output to the clinician that indicates the quality of contact of the electrodes 24. For example, as will be discussed below, the processing system 32 may provide information to the display device 40 that graphically represents the quality of contact of each of the electrodes 24.

As the basket structure 20 is moved through the anatomical structure, the processing system 32 continuously measures signals with the electrodes 24 to monitor any changes in the quality of contact with respect to each of the electrodes 24. In some embodiments, the processing system 32 updates the quality of contact of the electrodes 24 in real-time as the basket structure 20 is moved through the anatomical structure. In some embodiments, the display device 40 is configured to receive the updated quality of contact information from the processing system 32 and update the graphical display representative of the quality of contact of each of the electrodes 24 in real-time. The clinician may use this real-time updating to assure consistent quality contact with the anatomical structure is being made during the mapping procedure.

In addition, the clinician can identify anatomical landmarks or catheter orientation based on the graphical representation. For example, when mapping a cardiac structure, low amplitude signals would be expected as the electrodes 24 move past certain cardiac structures, such as valves. A clinician can rotate the basket structure 20 to see whether the low amplitude shift from electrodes 24 on one spline to electrodes 24 on another spline 44. The clinician can use this information to distinguish between an anatomical discontinuity and poor electrode contact.

When the electrodes 24 that are and are not making good contact with the anatomical structure have been identified, the processing system 32 may use this information to improve the visualization of physiological activity of the anatomical structure during mapping. For example, the processing system 32 may blank or ignore signals from electrodes 24 that are identified as making poor contact with the anatomical structure, since the signals sensed by these electrodes may be unreliable.

Figure 4:
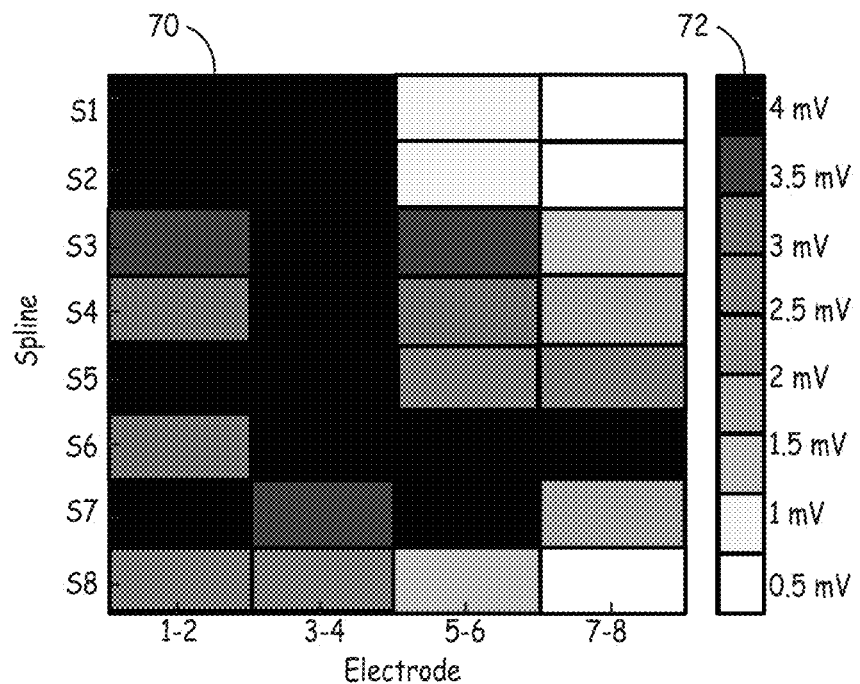
FIG. 4 is an illustration of a graphical display showing signal amplitudes for bipolar signals sensed by the plurality of mapping electrodes.

As discussed above, the display device 40 may be configured to display a graphical representation of the quality of contact of the electrodes 24. For example, FIG. 4 is an illustration of an embodiment of a graphical display showing signal amplitudes for bipolar signals sensed by the plurality of mapping electrodes 24. The display includes a panel 70 that depicts the bipolar signal amplitude measured by pairs of electrodes 24 on each of the splines 44. Particularly, the panel 70 shows bipolar signal amplitudes (in millivolts (mV)) across electrodes pairs E1-E2, E3-E4, E5-E6, and E7-E8 on each of the splines S1-S8. The scale 72 assigns a different color to each of the different bipolar signal amplitudes. In the embodiment illustrated in FIG. 4, the bipolar signal amplitude range displayed is from 0 mV to 4 mV. The electrode pairs with higher bipolar signal amplitudes indicate that the associated electrodes are in good contact with the anatomical structure, while the electrode pairs with lower bipolar signal amplitudes indicate that the associated electrodes are in poor electrical contact. Thus, in the illustrated example, if the amplitude threshold for good electrode contact is selected to be about 2 mV, the clinician may determine that electrode pairs E5-E6 on splines 51, S2, and S8 and electrode pair E7-E8 on splines S1-S4 and S8 are making poor contact. In an alternative embodiment, the clinician may set the display device 40 to display electrodes 24 making good contact, as determined by a threshold signal value, in a first color and electrodes 24 making poor contact in a second color.

Figure 5:
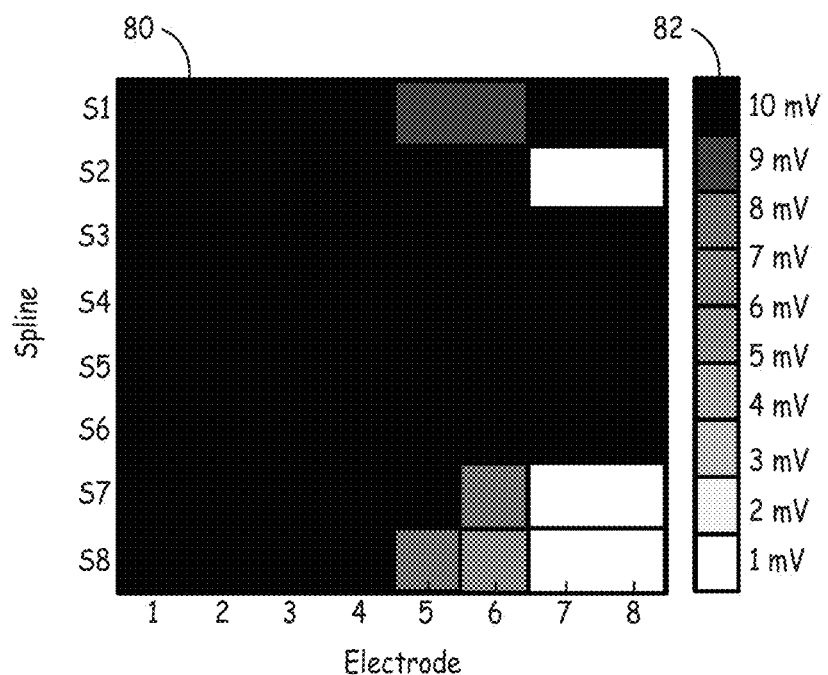
FIG. 5 is an illustration of a graphical display showing signal amplitudes for unipolar signals sensed by the plurality of mapping electrodes.

FIG. 5 is an illustration of an embodiment of a graphical display showing signal amplitudes for unipolar signals sensed by the plurality of mapping electrodes 24. The display includes a panel 80 that depicts the unipolar signal amplitude measured by each electrode 24 on each of the splines 44. Particularly, the panel 80 shows unipolar signal amplitudes (in millivolts (mV)) at each electrode E1-E8 on each of the splines S1 -S8. The scale 82 assigns a different color to each of the different unipolar signal amplitudes ranging from 0 mV to 10 mV. The electrodes 24 with higher unipolar signal amplitudes indicate that the electrodes 24 are in good contact with the anatomical structure, while the electrodes 24 with lower unipolar signal amplitudes indicate that the electrodes 24 are in poor electrical contact. Thus, in the illustrated example, if the amplitude threshold for good electrode contact is set at about 2 mV, the clinician can determine that electrodes E7 and E8 on splines S2, S7, and S8 are making poor contact with the anatomical structure. In an alternative embodiment, the clinician may set the display device 40 to display electrodes 24 making good contact, as determined by a threshold signal value, in a first color and electrodes 24 making poor contact in a second color.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

We claim:
1. A catheter system comprising:
   a catheter including (1) a contact determination mechanism, the contact determination mechanism comprising a force sensor; and (2) a plurality of mapping electrodes, each mapping electrode configured to sense signals associated with an anatomical structure; and a processor operatively coupled to the plurality of mapping electrodes and configured to:
receive the signals sensed by the plurality of mapping electrodes;
determine a signal parameter associated with each of the plurality of mapping electrodes;
determine a quality of contact of each of the plurality of mapping electrodes with the anatomical structure based on the signal parameter and an output of the contact determination mechanism; and
generate a map of the anatomical structure based only on electrodes having sensed signals with a quality of contact exceeding a threshold value, wherein the sensed signals include sensed signals with a quality of contact exceeding a threshold value and sensed signals with a quality of contact not exceeding the threshold value.

2. The catheter system of claim 1, further comprising a display device configured to provide a graphical display representative of the quality of contact of the plurality of mapping electrodes.

3. The catheter system of claim 1, wherein the processor is further configured to generate a map of the anatomical structure based on electrodes having sensed signals with amplitudes greater than a threshold amplitude.

4. The catheter system of claim 1, wherein the processor is configured to sense and characterize at least one of unipolar signals and bipolar signals.

5. The catheter system of claim 1, wherein the catheter comprises an ablation catheter.

6. The catheter system of claim 1, wherein the processor is further configured to identify contours of the anatomical structure based on the quality of contact of the plurality of mapping electrodes.

7. The catheter system of claim 1, wherein the processor is further configured to determine an orientation of the plurality of mapping electrodes based on the quality of contact of the plurality of mapping electrodes.

8. A method for mapping an anatomical structure, the method comprising:
sensing signals associated with an anatomical structure with a plurality of mapping electrodes;
characterizing the signals sensed by the plurality of mapping electrodes based on a signal parameter associated with the plurality of mapping electrodes;
determining a quality of contact of the plurality of mapping electrodes with the anatomical structure based on the signal characterization, wherein the determining step comprises combining the signal characterization with an output of a contact determination mechanism, the contact determination mechanism comprising a force sensor; and
generating a map of the anatomical structure based only on electrodes having sensed signals with a quality of contact exceeding a threshold value, wherein the sensed signals include sensed signals with a quality of contact exceeding a threshold value and sensed signals with a quality of contact not exceeding the threshold value.

9. The method of claim 8, further comprising generating a map of the anatomical structure based only on electrodes having sensed signals with amplitudes greater than a threshold amplitude.

10. The method of claim 8, further comprising identifying contours of the anatomical structure based on the quality of contact of the plurality of mapping electrodes.

11. The method of claim 8, further comprising determining an orientation of the plurality of mapping electrodes based on the quality of contact of the plurality of mapping electrodes.

12. A method for mapping an anatomical structure, the method comprising:
positioning a plurality of mapping electrodes proximate to an anatomical structure;
sensing signals with the plurality of mapping electrodes;
characterizing the signals sensed by the plurality of mapping electrodes based on a signal parameter associated with the mapping electrodes;
determining a quality of contact of the plurality of mapping electrodes with the anatomical structure based on the signal characterization, wherein the determining step comprises combining the signal characterization with an output of a contact determination mechanism, the contact determination mechanism comprising a force sensor;
displaying a graphical display representative of the quality of contact of the plurality of electrodes;
repositioning the plurality of mapping electrodes with respect to the anatomical structure;
updating the graphical display in real-time as the quality of contact of the plurality of electrodes changes when the plurality of electrodes are repositioned; and
generating a map of the anatomical structure based only on electrodes having sensed signals with a quality of contact exceeding a threshold value, wherein the sensed signals include sensed signals with a quality of contact exceeding a threshold value and sensed signals with a quality of contact not exceeding the threshold value.

13. The method of claim 12, wherein the sensing step comprises sensing bipolar signals with the pairs of the plurality of mapping electrodes.

14. The method of claim 12, wherein the sensing step comprises sensing unipolar signals with each of the plurality of mapping electrodes.

15. The method of claim 12, and further comprising generating a map of the anatomical structure based only on electrodes having sensed signals with amplitudes greater than a threshold amplitude.

* * * * *